(12) United States Patent
Russell et al.

(10) Patent No.: US 6,270,761 B1
(45) Date of Patent: Aug. 7, 2001

(54) DELIVERY OF NUCLEIC ACID

(75) Inventors: Stephen James Russell, Cambridgeshire; Frances Joanne Morling, Cambridge, both of (GB)

(73) Assignee: Cambridge Drug Discovery Holdings, LTD, Cambridge (GB)

( * ) Notice: Subject to any disclaimer, the term of this patent is extended or adjusted under 35 U.S.C. 154(b) by 0 days.

(21) Appl. No.: 09/000,103
(22) PCT Filed: Jul. 23, 1996
(86) PCT No.: PCT/GB96/01764
§ 371 Date: Jun. 29, 1998
§ 102(e) Date: Jun. 29, 1998
(87) PCT Pub. No.: WO97/05264
PCT Pub. Date: Feb. 13, 1997

(30) Foreign Application Priority Data

Jul. 26, 1995 (GB) .................................................. 9515356

(51) Int. Cl.[7] .............................. A61K 48/00; C12N 15/88
(52) U.S. Cl. ..................... 424/93.2; 435/320.1; 435/325; 435/455; 514/44
(58) Field of Search .............................. 514/44; 435/455, 435/320.1, 325; 424/93.2

(56) References Cited

U.S. PATENT DOCUMENTS

| | | | |
|---|---|---|---|
| 5,484,720 | * | 1/1996 | Wurm et al. .......................... 435/455 |
| 5,547,932 | * | 8/1996 | Curiel et al. ........................... 435/65 |
| 5,633,156 | * | 5/1997 | Wurm et al. .......................... 435/455 |

FOREIGN PATENT DOCUMENTS

| | | |
|---|---|---|
| WO 94/11524 | 5/1994 | (WO) . |
| WO 96 7750 A1 | 3/1996 | (WO) . |

OTHER PUBLICATIONS

Wilson et al, Anal. Biochem., vol. 226, No. 2, pp. 212–220, Apr. 10, 1995.
Ishiura et al, Mol. Cell. Biol., vol. 2, No. 6, pp. 607–616, Jun., 1982.
Pear et al, Proc. Natl. Acad. Sci., vol. 90, pp. 8392–8396, Sep., 1993.
Morling et al, Gene Therapy, vol. 2, No. 7, pp. 504–508, Sep., 1995.
Jordan et al, Nucleic Acid Research, vol. 24, No. 4, pp. 596–601, Feb., 1996.
Wagner et al, Advanced Drug Deliver Reviews, vol. 14, pp. 113–135, 1994.
Carstens et al, Virology, vol. 101, No. 1, pp. 311–314, 1980.
Thrasher et al, The Lancet, vol. 346, No. 8967, pp. 92–93, Jul., 1995.
Von Ruden et al, Boitechniques, vol. 18, No. 3, pp. 484–489, Mar., 1995.
Chen et al, Biotechniques, Vo. 6, No. 7, pp. 632–638, 1988.
Derwent Publications, AN 94–156567, Apr. 12, 1994.
Kamik et al, Arch. Microbiol., vol. 136, No. 4, pp. 275–280, 1983.

\* cited by examiner

*Primary Examiner*—Dave Nguyen
(74) *Attorney, Agent, or Firm*—Kathleen M. Williams; Palmer & Dodge, LLP (57) ABSTRACT

Disclosed are various compositions for use in the delivery of nucleic acid to a target cell including: a composition comprising a calcium salt in particulate form, the nucleic acid to be delivered, and one or more further components to enhance the efficiency of delivery of the nucleic acid to a target cell, the nucleic acid and the one or more further components being complexed with the particulate calcium salt; and methods of delivering a nucleic acid to a target cell.

16 Claims, 4 Drawing Sheets

DELIVERY OF NUCLEIC ACID

This application is the national phase of international application PCT/GB96/01764 filed Jul. 23, 1996 which designated the U.S.

FIELD OF THE INVENTION

This invention relates to the fields of gene transfer and therapy, scaled production of viral vectors and vaccines, and virus detection. The invention provides for methods which increase the efficiency of virus adsorption to mammalian cells, useful for virus detection and for enhancing the gene transfer efficiencies of viral and plasmid vectors. It also provides for a simple method to concentrate/purify retroviral or adenoviral vectors. In particular, the invention relates to compositions for delivering a nucleic acid to a target cell, methods of making such compositions, and to a method of delivering nucleic acid to a target cell.

BACKGROUND TO THE INVENTION

Murine leukaemia virus—derived retroviral vectors are being used in clinical gene therapy trials for ex vivo transduction of T cells, hepatocytes, haemopoietic stern cells, synoviocytes, fibroblasts and a variety of neoplastic cells (Human gene marking/therapy clinical protocols, 1994 Hum. Gene Ther. S p417–426: Clinical protocols. 1994 Cancer Gene Ther. I p73–78). However, low frequency of target cell transduction is proving to be a serious limiting factor in these early trials (Rosenberg et al. 1990 N. Engl. J. Med. 323 p570–578; Brenner et al, 1993 Lancet 341 p85–88; Grossman et al, 1994 Nat. Genet. 6 p335–341; Rill et al, 1994 Blood 84 p380–383).

The efficiency of retroviral gene transfer is influenced by a number of factors including the concentration and physical integrity of the virus particles and the concentration, proliferative activity and inherent susceptibility of the target cells (Vile & Russell, 1995 Brit. Med. Bulletin 51 p12–30). Local conditions affecting the kinetics of virus adsorption to target cell membranes also have a major influence on retroviral titres. Polybrene is used routinely to enhance the adsorption of retroviral vectors and usually increases the titre severalfold. However, during 2-hour incubations of MLV-derived retroviral vectors with target cells in standard conditions (i.e. with added polybrene) only a small percentage (ea. 5%) of the infectious various were depleted from the medium indicating that virus adsorption is highly inefficient (i.e. slow rate of adsorption) even in the presence of polybrene (Wang et al, 1991 J. Virol, 65 p6468–6477). The kinetics of virus adsorption are likely to be equally slow for other viruses in similar ex vivo tissue culture systems. Low speed centrifugation of unprecipitated retroviral vectors onto their target cells has been shown to enhance transduction efficiencies, presumably by speeding the rate of specific virus adsorption (Kotani et al, 1994 Hum. Gene Ther. S p19–28).

Chromatography on calcium phosphate (hydroxyapatite) columns has previously been used to purify and concentrate proteins (Tiselius et al, 1956 Arch. Biochem. Biophys. 65 p132–155), DNA (Main & Cole, 1957 Arch. Biochem. Biophys, 68 p186), RNA (Semenza, 1957 Biochim. Biophys. Acta 24 p401) and viruses (Taverne et al, 1958 I. Gen. Microbiol. 19 p451–461).

Influenza virus purification has also been achieved by adsorption on a precipitate of calcium phosphate formed by adding calcium chloride to a phosphate-containing solution (Salk. 1941 Proc. Soc. Exp. Biol. Med. 46 p709–712; Stanley, 1945 Science 101 p332–335). To purify the virus, the washed precipitate was redissolved in citric or hydrochloric acid and dialysed against distilled water. There was little, if any, loss in virus infectivity during the process of washing, elution and dialysis (Salk, 1941 Proc. Soc. Exp. Biol. Med. 46p709–712). To secure the most effective precipitation of virus, it was necessary to carry out the formation of the calcium phosphate precipitate in the presence of the virus (Stanley, 1945 Science 101 p332–335). The infectivity of viruses still bound to calcium phosphate was not tested and there are no reports of attempts to purify retroviruses in this way. Also, there are no reports of attempts to enhance viral gene transfer by presenting viruses to cells as a complex with precipitated calcium phosphate.

DNA adsorbs to calcium phosphate formed when calcium chloride is added to a phosphate-containing solution and this provides the basis of a widely used technique for introducing foreign DNA into mammalian cells (Graham & van der Eb, 1973 Virology 52p456–467). The mechanism of DNA uptake by this method has been studied in detail using fluorescent dyes to independently follow the fates of the DNA and of the calcium phosphate (Loyter et al, 1982 Proc. Natl. Acad, Sci, USA 79 p422–426). The DNA forms a tight complex with the calcium phosphate and the DNA in the complex is resistant to nucleases. The calcium phosphate increases the concentration of DNA on the cell surface by precipitation, induces endocytosis, facilitating entry of DNA into cells, and protects the DNA from degradation by intracellular nucleases. Cellular uptake of the calcium phosphate—DNA complexes is highly dependent upon the pH at which they are formed and upon the concentration of DNA in the complex. However, only a small proporation of the DNA that has been taken up by the cell moves from the cytoplasm to the nucleus. Hence the efficiency of gene expression after DNA transfection remains very low.

Molecular conjugate vectors were developed to overcome some of the limitations of previous nonviral gene delivery systems. The major limitation with calcium phosphate transfection was the inefficiency with which DNA delivered as a calcium phosphate co-precipitate could escape from endosomal vesicles into the cytosol. In molecular conjugate vectors, receptor-mediated endocytosis of the DNA is achieved by complexing it to a macromolecular ligand and escape from the endosome is achieved by adding an endosomolytic agent to the complex, such as an adenovirus particle (Michael & Curiel, 1994 Gene Therapy I p223–232).

The endosomolytic properties of adenovirus particles have also been harnessed to facilitate gene transfer by retroviral vectors to cells outside of their normal host range (Adams et al 1995 J. Virol, 69 p1887–1894). In the presence of adenovirus, several different ecotropic retroviral vectors were shown to infect human cell lines and a xenotropic vector was shown to infect marine cells. However, in these experiments there was no attempt to achieve physical linkage between the adenovirus and retrovirus particles before they were placed in contact with the target cells.

SUMMARY OF THE INVENTION

In a first aspect the invention provides a composition for delivering a nucleic acid to a target cell, comprising: a calcium salt in particulate form; the nucleic acid to be delivered; and one or more further components to enhance the efficiency of delivery of the nucleic acid to a target cell; the nucleic acid and the one or more further components being complexed with the particulate calcium salt.

In a second aspect the invention provides a composition for delivering a nucleic acid to a target cell, comprising the nucleic acid to be delivered, an endosomolytic moiety, and a calcium salt in particulate form. Preferably the calcium salt is complexed with the other components of the composition.

Preferably the one or more further components of the composition of the first aspect conveniently comprise components which improve the specificity of uptake of the nucleic acid (i.e. they may tend to target the nucleic acid to the target cell). Examples of such components include members of specific binding pairs which are capable of binding to receptor molecules expressed on the surface of the target cell, such as the growth factors detailed in WO94/27643. The one or more further components may additionally or alternatively serve to alter the solubility of the complex in aqueous conditions. Preferably such components would increase the solubility of the complex.

Desirably the one or more further components of the composition of the first aspect comprise an endosomolytic moiety. Such an endosomolytic moiety present in a composition in accordance with the first or second aspects of the invention may conveniently be an adenovirus particle or an effective portion thereof.

Desirably the nucleic acid to be delivered, by a composition according to the first or second aspect of the invention, is packaged within a vector particle. In a third aspect the invention provides a composition for delivering a nucleic acid to a target cell, the composition comprising the nucleic acid to be delivered packaged within a vector particle, said vector particle being complexed with a calcium salt in particulate form.

Preferably a composition in accordance with any one of the aspects defined above will comprise the nucleic acid to be delivered packaged within a viral particle, desirably a retroviral particle (especially a C type retroviral particle) and, in particular, an MLV retroviral particle.

The particulate calcium salt present in a composition in accordance with any one of the aspects defined above is preferably calcium phosphate and typically will be present in substantially crystalline form.

The present invention is based, at least in part, on the surprising finding that viral particles, especially retrovirus and adenovirus particles, are able to bind rapidly and efficiently to calcium phosphate crystals and remain fully infectious whilst complexed therewith.

The present inventors have also found that calcium phosphate crystals have several properties that make them especially useful as vehicles for delivering nucleic acids (in particular, genes, or other portions of DNA, such as plasmids or parts thereof) to cells, especially eukaryotic cells. In particular the compositions comprising calcium phosphate are useful for delivering genes to mammalian cells in culture. The crystals' high density causes them to settle rapidly onto cells. Their small size allows endocytosis from the surface of cells. Their acid solubility, presumably allows dissolution in acidified endosomers so the cell does not retain the crystal as a foreign body. Their high affinity for nucleic acids and ability to protect nucleic acids from nuclease digestion facilitates their use for carriage of DNA or RNA into endosomes. A further advantage of the use of calcium phosphate crystals as nucleic acid delivery vehicles is the possibility of enhancing delivery (of gene therapy vectors, for example) to a particular in vivo microenvironment. For example, aerosolised calcium phosphate crystals might penetrate into small airways more effictively than aerosolised viruses or liposomes, allowing more efficient gene transfer to small airway epithelium.

One limitation of calcium phosphate crystals is that they do not provide, per se, any mechanism for the endocytosed DNA or RNA to escape from the endosomes. Therefore, based on the inventors' novel observation that they also have a high affinity for endosomolytic adenovirus particles, it is preferred to prepare calcium phosphate/nucleic acid/endosomolytic moiety complexes in which the endosomolytic moiety (typically an adenovirus) will facilitate endosomal escape of the nucleic acid. This will greatly enhance the efficiency with which the nucleic acid is translocated to the cell nucleus. As an alternative to the use of adenovirus, it should also be possible to incorporate purified endosomolytic proteins into calcium phosphate-nucleic acid complexes, since calcium phosphate also has a high affinity for proteins. Many endosomolytic proteins are known (see for example Plank et al., 1994 J. Biol. Chem. 269, 12,918–12,924).

In a fourth aspect the invention provides a method of making a composition for delivering a nucleic acid to a target cell, comprising mixing a calcium salt in particulate form with a nucleic acid to be delivered so as to form a complex. Preferably the nucleic acid is packaged within a viral vector particle, as defined above. Conveniently one or more further components may be included (such as endosomolytic or targeting moieties, as defined previously) in the complex.

Preferably the complex is formed by co-precipitation of the components, typically by the addition of a calcium salt to a mixture comprising a phosphate salt, so as to cause the precipitation of calcium phosphate. The calcium salt added is conveniently calcium chloride.

Conveniently the precipitated complex is harvested by centrifugation. Advantageously, the complex may be formed and centrifuged in situ in the presence of target cells to which the nucleic acid is to be delivered, thereby recovering the complex and contacting it with target cells in single step.

In a fifth aspect, the invention provides a method of delivering a nucleic acid to a target cell, comprising the use of a composition in accordance with any one of the first, second or third aspects of the invention.

Desirably the method comprises the formation of the composition is situ and contacting the composition with target cells in a single step. Conveniently contact between the composition and the target cell can be improved by subjecting the composition/target cell mixture to centrifugation.

In a further aspect, the invention provides a method of detecting the presence of an infectious agent in a sample, comprising mixing the sample with a calcium salt in particulate form (typically crystalline calcium phosphate) so as to form a complex comprising the infectious agent and the particulate calcium salt, and contacting the complex with a plurality of target cells, at least some of which are capable of being infected by the infectious agent, and detecting cells which become infected.

The infectious agent is typically a virus. A number of methods of detecting infection of a cell are known. These include, for example, ,microscopic examination of cultured cells for cytopathic effects, or probing cells with reagents (e.g. antibodies) specific for components of the infectious agent (which will be amplified in the infected cells compared to the amount present in the original sample).

In a further aspect the invention provides a kit for use in delivering a nucleic acid to a target cell, comprising a solution of calcium chloride, or means for making same, and instructions for performing the method of making a composition as defined above. Preferably the kit will further comprise one or more of the following components, a nucleic acid to be delivered to the target cell; an endosomolytic moiety; a targeting moiety for targeting the nucleic acid to the target cell; and a plurality of target cells. Typically the further components will be included as part of another component of the composition (e.g. packaged within a viral particle), but may be present as discrete entities.

The present inventors have been able to devise a simple method to enhance the efficiency of ex vivo gene transfer, especially retroviral-mediated transfer (example 1). In one embodiment, calcium chloride is added to the vector stock (containing phosphate salts) and calcium phosphate precipitates out of solution, forming a complex with the retroviral vectors. When such calcium phosphate-retroviral vector complexes are used for gene transfer, the vector titres are increased at least five-fold, and can be increased as much as fifty-fold compared to the titres obtained in standard polybrene-enhanced infection protocols. Titre enhancement is independent of the starting concentration of vector, is equally effective for ecotropic and amphotropic retroviral vectors on a variety of mouse and human cells, and is not associated with any alteration in vector host range properties. The retrovirus particles contained in a large volume of supernatant can be rapidly concentrated/purified by co-precipitation with calcium phosphate followed by low-speed centrifugation and dissolution of the pelleted precipitate in a smaller volume.

The inventors have also shown that the method can be used for efficient precipitation and titre enhancement of adenovirus particles as a complex with calcium phosphate (see example 2 below). The adenovirus particles remain fully infectious whilst complexed to the calcium phosphate.

Also, in light of the observation that the endosomolytic properties of adenovirus particles can be employed to facilitate gene transfer by retroviral vectors to cells outside of their normal host range (Adams et al 1995 J. Virol. 69 p-1894), it is proposed to prepare calcium phosphate-retrovirus-adenovirus complexes (e.g. co-precipitates) in which the calcium phosphate will facilitate contact with the target cells and carriage of the viruses into the endosomal compartment, and the adenovirus moiety will facilitate endosomal escape of the endocytosed retrovirus.

Co-precipitation of retroviral or adenoviral vectors as a complex with calcium phosphate can be used to concentrate/purify the vectors from large volumes of culture supernatant, avoiding the need for high speed centrifugation of such large volumes which is costly and inconvenient. The precipitation step could be incorporated at various stages in the production cycle.

A second application is to use the calcium phosphate crystals as virus carriers to speed the kinetics of virus/vector adsorption to target cells, thereby enhancing the efficiency of gene transfer (e.g. in gene therapy protocols where cells are transduced outside the body). Polybrene is not needed when this strategy is employed to enhance gene transfer efficiency so it may be especially useful for transduction of cells which are intolerant of exposure to polybrene.

The invention will now be further described by way of illustrative example and with reference to the accompanying drawings, of which.

EXAMPLE 1

Materials and Methods

Cell Lines.

Retroviral vector producer cells (kindly provided by Dr F-L Cosset) were derived from the TELacZ.6 line (Takeuchi et al 1994 J. Virol. 68 p 8001–8007) by stable transfection with plasmids expressing MoMLV (Moloney murine leukaemia virus) gag and pol proteins and either Maloney (ecotropic) or 4070A (amphotropic) envelopes. Retroviral particles produced by these cells package the MGFnlsLacZ reporter retroviral vector, are free of helper virus and transfer a functional β-galactosidase gene.

The retroviral produced cells, the NIH3T3 mouse fibroblast line, the A431 human epidermoid carcinoma (Giard et al 1973 J. Natl. Cancer, Inst. 51 p1417–1421), the EJ bladder carcinoma (Bubenik et al 1973 Int. J. Cancer. 11 p765–773) and the C170 colon carcinoma (provided by Dr M J Embleton:-(Pimm et al 1990 Br. J. Cancer. 61 p508–513)) cell lines were grown in DMEM (Gibco-BRL) supplemented with 10% Foetal Calf Serum (PAA Biologicals), 60 μg/ml benzyl penicillin and 100 μg/ml streptomycin at 37° C. in an atmosphere of 5% $CO_3$. The human B cell lymphoma line K422 (Dyer, et al 1990 Blood 75 p709–714) was grown in RPMI 1640 (Gibco-BRL) supplemented with 10% FoetaL Calf Serum, 60 μg/ml benzyl penicillin and 100 μg/ml streptomycin at 37° C. in an atmosphere of 5% $CO_2$.

Production of retroviral vectors.

Vector producer cells were expanded at 37° C. in an atmosphere of 5% $CO_2$ and, once confluent were moved to a 32° C. incubator and maintained for 72 hrs. Supernatants containing retroviral vectors were harvested after overnight (16 hrs) incubation at 32° C. in serum free DMEM and filtered (0.45 µm) before addition of CaCl and infection of cells. Fresh supernatants were used for all experiments.
Co-precipitation of retroviral vectors.

Small volumes of 1M $CaCl_2$ were added to filtered retroviral vector supernatants to increase the concentration of $CaCl_2$ by 1 to 10 mmol/l (5 mmol/I in the 'standard' protocol). The $CaCl_2$-adjusted retroviral vector supernatants were then incubated at room temperature of 37° C. for a variable time (30 minutes 'standard') to allow precipitate formation. To harvest precipitates, 1 ml aliquots of the $CaCl_2$-treated vector supernatant was microfuged for 1 min at 13,000 rpm, the cleared supernatant was removed and the pellet resuspended in 1 ml fresh DMEM. To harvest the precipitate from a larger volume (10 ml) of retroviral vector supernatant, the supernatant was treated with 5 mmol/l $CaCl_2$, centrifuged in an IEC Centra-8R Centrifuge (1500 rpm. 10 mins. 4° C.) and the pellet was redissolved in 100 µl 0.5M EDTA, dilutions of which were used for infection assays.
Infection assays.

Cells to be infected were seeded at $2 \times 10^5$ cells/well in six-well plates (Corning) and incubated at 37° C. overnight in their regular medium. Dilutions of (untreated or co-precipitated) β-galactosidase-transducing retroviral vectors in 2 mls serum-free DMEM were added to cells in the presence or absence of 8 µg/ml polybrene for 2–6 hours (2 hours as standard). The retroviral vector supernatant was removed, the cells washed once with PBS and incubated in regular medium for 48–72 hrs. $CaCl_2$-treated supernatants were mixed vigorously to ensure even suspension of the precipitate before aliquots were removed for dilution or direct application to target cells.

X-gal staining for detection of β-galacotosidase activity was performed as previously described (Takeuchi et al 1994 J. Virol 68 p8001–8007). Cells were filled with 0.5% glutaraldehyde in PBS at room temperature for 10 min. washed once with PBX and incubated overnight at 37° C. with a 0.2 µui-filtered solution containing 1mg/ml 5-bromo-4-chloro-3-indoyl-β-D-galactoside (X-gal) in 5 mM potassium ferricyanide, 5 mM potassium ferrocyanide and 2 mM $MgCl_2$. Viral titre was calculated by counting blue colonies microscopically with the use of a grid placed underneath the 6-well plate.

RESULTS

Co-precipitation of retroviral vectors

When $CaCl_2$ was added to DMEM, into which β-galactosidase-transducing retroviral vectors had been harvested, a fine precipitate of calcium phosphate formed. The precipitate formed more rapidly, and in greater abundance, as progressively larger amounts of $CaCl_2$ were added (up to 10 mmol/l) and settled slowly to the bottom of the tube or could be rapidly sedimented by centrifugation. The precipitate was first visible 6 hours after the addition of 1 mmol/l $CaCl_2$, one hour after the addition of 2 mmol/l $CaCl_4$ and less than 30 minutes after the addition of 3–10 mmol/l $CaCl_2$.

Figure 1:
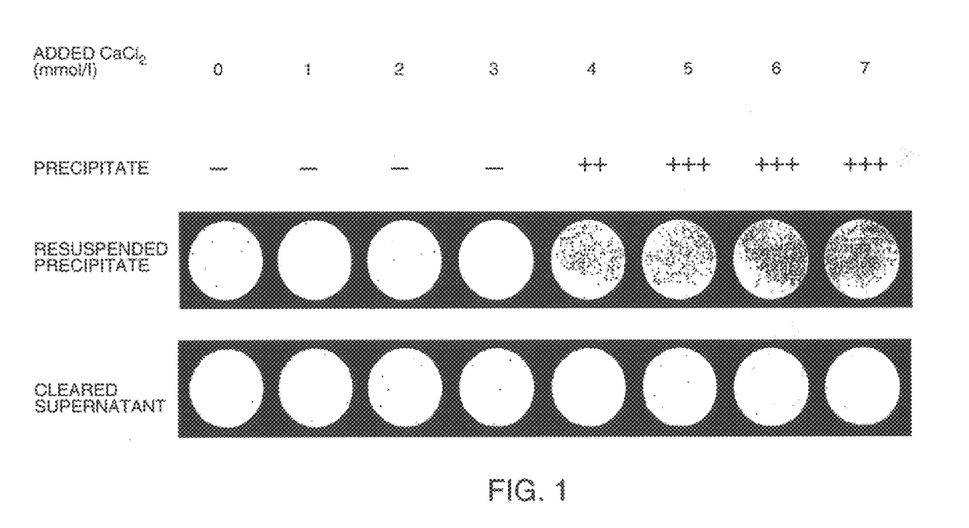
FIG. 1 shows co-precipitation of retroviral vectors with calcium phosphate. Increasing amounts of $CaCl_2$ were added to 1 ml aliquots of amphotropic vector stock, incubated for 30 minutes, microfuged and the pelleted precipitate of calcium phosphate was resuspended in 1 ml DMEM. The β-galactosidase-transducing activity in 10 μl of the resuspended precipitate versus 10 μl of the cleared supernatant was compared by infection of NIH 3T3 cells. Stained plates were photographed without magnification. The amount of precipitate formed at various concentrations of $CaCl_2$ was assessed microscopically on a scale of—(no visible precipitate) to +++ (abundant)

To determine whether the retroviral vectors were co-precipitated as a complex with the calcium phosphate, increasing amounts of $CaCl_2$ were added to aliquots of an amphotropic retroviral vector stock and 30 minutes later the precipitates were harvested by centrifugation, resuspended in DMEM and used to infect NIH 3T3 cells. FIG. 1 shows that the great majority of β-galactosidase transducing retroviral vectors were recovered in the resuspended precipitate and that less than 1% of the total remained in the cleared supernatant.

To further demonstrate the co-precipitation of retroviral vectors, we added 5 mmol/l $CaCl_2$ to 10 mls of ecotropic vector stock, pelleted the precipitate, redissolved it in 200 µl 5M EDTA and compared the vector titres (β-galactosidase e.f.u. on NIH 3T3 cells) before and after concentration. The titre increased 25-fold from $2 \times 10^3$ e.f.u. per ml to $5 \times 10^6$ e.f.u. per ml after concentration indicating that the vector particles were efficiently co-precipitated and were not damaged in the process.

Enhanced Titre of Co-precipitated Retroviral Vectors

Figure 2A:
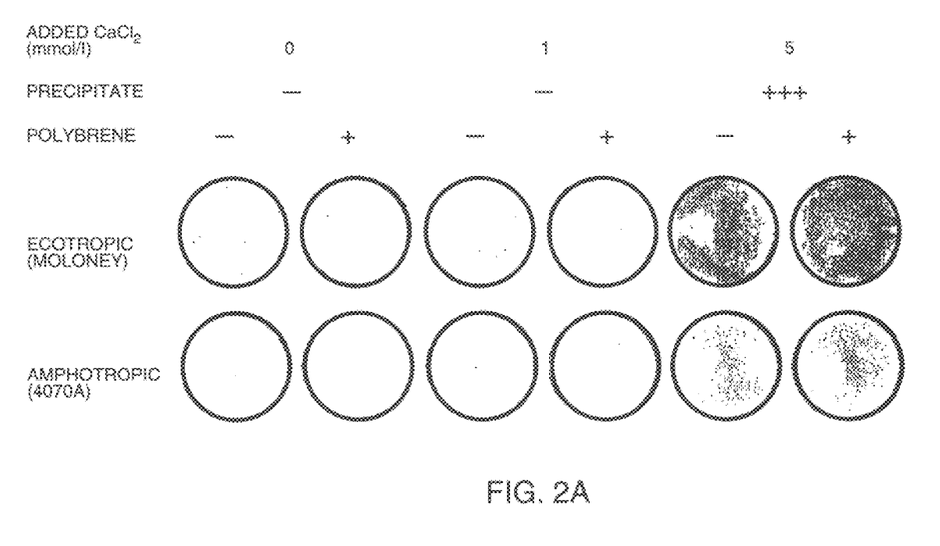
FIGS. 2A and 2B show enhanced titre of co-precipitated retroviral vectors on NIH 3T3 cells. Increasing amounts of $CaCl_2$ were added to β-galactosidase-transducing vector stocks and, after a 30 minute incubation, 10 μl of the treated stock was used to infect NIH 3T3 cells (2 hour incubation in a final volume of 2 mls) with or without added polybrene. A. photographic record showing β-gal activity of NIH 3T3 infected with ecotropic and amphotropic vectors. The precipitate was quantitated as in FIG. 1 legend. B. Titre of amphotropic vector (in β-galactosidase-transducing units per ml of supernatant) is plotted against concentration of $CaCl_2$.
Figure 2B:
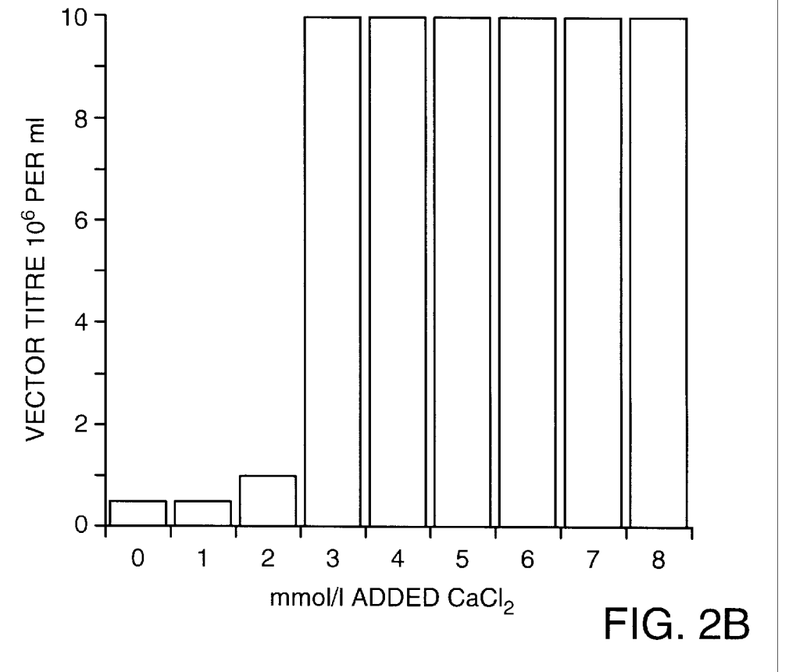

We next explored the possibility that calcium phosphate co-precipitation might be used to concentrate vector particles directly onto their larger cells, thereby enhancing the apparent titre of a retroviral vector stock. Increasing amounts of $CaCl_2$ were added to ecotropic and amphotropic retroviral vector stocks (in DMEM) 30 minutes before they were titred on NIH 3T3cells. FIG. 2 shows that this simple procedure could enhance retrovirus titre as much as 50-fold compared to the standard polybrene-enhanced infection protocol. In these experiments the addition of at least 3 mmol/l $CaCl_2$ was required for maximal titre enhancement but the same effect could be achieved at lower concentrations of $CaCl_2$ by extending the period of time allowed for formation of the precipitate (data not shown). A second point to emerge from the results shown in FIG. 2a is that when retroviral vectors are presented to cells as a calcium phosphate co-precipitate, polybrene has little additional effect on their enhanced infectivity.

In the experiments described above, the volume of co-precipitated vector added to the cells (10 µl) was insufficient to influence the $CaCl_2$ concentration in the culture medium (2 mls) at the time of infection. Increasing amounts of $CaCl_2$ were therefore added to the culture medium during a 2-hour incubation with vectors (10 µl) that had been precipitated by adding 5 mmol/l $CaCl_2$. Further (two to three-fold) enhancement of the titre was observed only at low ambient concentrations of $CaCl_2$ and was maximal upon addition of 1 mmol/l (data not shown).

Figure 3:
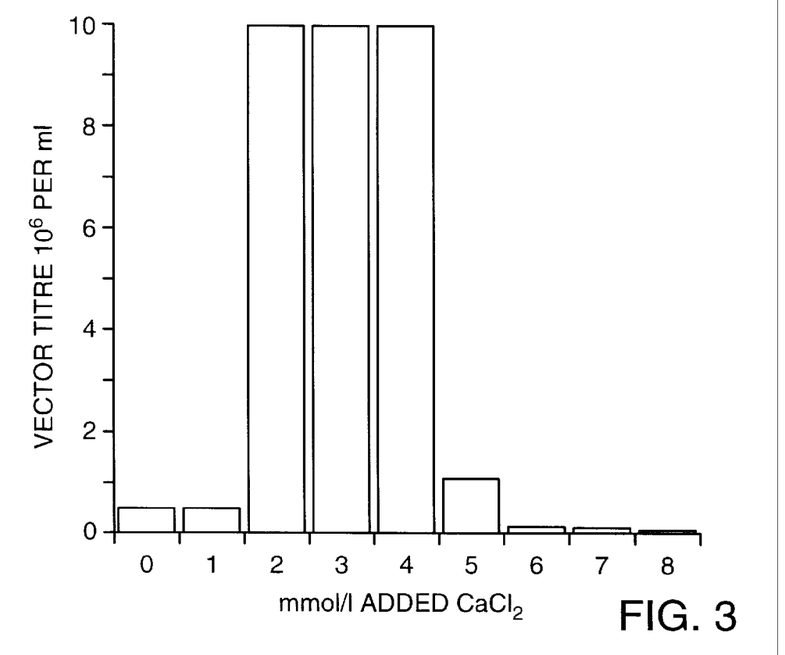
FIG. 3 is a graph showing enhanced titre of retroviral vectors co-precipitated onto NIH 3T3 cells during infection. Amphotropic β-galactosidase-transducing vector stock was diluted in DMEM and used to infect NIH 3T3 cells (2 hour incubation in a final volume of 2 mls with added polybrene). Increasing amounts of $CaCl_2$ were added to the medium at the start of the infection protocol. Titre (in β-galactosidase-transducing united per ml of supernatant) is plotted against concentration of $CaCl_2$.

We then explored alternative infection protocols in which increasing amounts of $CaCl_2$ were added to the culture medium in contact with NIH 3T3 cells during a 2-hour incubation with vectors that had not been precipitated beforehand. FIG. 3 shows a typical result in which the titre is maximally enhanced following the addition of 2 to 4 mmol/l $CaCl_2$. The inhibition seen at higher concentrations of $CaCl_2$ is due at least in part to a cytotoxic effect, possible the consequence of excessive precipitate formation. With longer incubation times, this cytotoxic effect became more pronounced and was seen at lower concentrations of $CaCl_2$ (data not shown).

To determine whether the efficiency of retroviral vector precipitation was influenced by the starting concentration of vector particles, we made serial dilutions (ranging from 1 to $10^\circ$ β-galactosidase-transducing unites per ml) of an amphotropic retroviral vector in DMEM and compared the titres of co-precipitated (5 mmol/l $CaCl_2$) and unprecipitated dilutions. The titre of the co-precipitated vector was enhanced to approximately the same extent (5-fold to 15-fold) at every dilution tested.

Host Range Properties of Co-precipitated Retroviral Vectors

We suspected that efficient gene transfer by co-precipitated retroviral vectors was a gravitational phenomenon, the insoluble calcium phosphate serving to bring vector particles into close contact with target cells at the bottom of the culture dish. However, it seemed possible that the precipitate might also facilitate a novel mechanism of retrovirus entry which would be manifest as an extension of the normal host range. We therefore tested the infectivity (on mouse and human cells) of co-precipitated retroviral vector particles bearing ecotropic envelopes (Table I). The ecotropic host range of the precipitated vectors was well maintained and there was no increase in the background level of gene transfer to human cells. We also tested the infectivity of co-precipitated retroviral particles that were devoid of envelope glycoproteins and in this case the only effect of precipitation was a slight increase in the background level of gene transfer (Table I)

Table I. Host range properties of co-precipitated retroviral vectors.

Unprecipitated and precipitated (5 mmol/l added $CaCl_2$, 30 minutes incubation) β-galactosidase-transducing vector stocks were titrated on murine and human cell lines. Titre were shown at lacZ efu/ml. ND=not done.

| | ECOTROPIC (Moloney) | | ENVELOPE AMPHOTROPIC (4070A) | | NONE | |
|---|---|---|---|---|---|---|
| | Added $CaCl_2$ (mmol/L) | | | | | |
| Cell Line | 0 | 5 | 0 | 5 | 0 | 5 |
| NIH3T3 (Mouse) | $10^6$ | $2 \times 10^7$ | $10^6$ | $2 \times 10^7$ | 2 | 32 |
| A431 (Human) | 0 | 0 | $10^6$ | $2 \times 10^7$ | N.D. | N.D. |
| FI Human | 0 | 0 | $5 \times 10^5$ | $5 \times 10^6$ | N.D. | N.D. |

Figure 4:
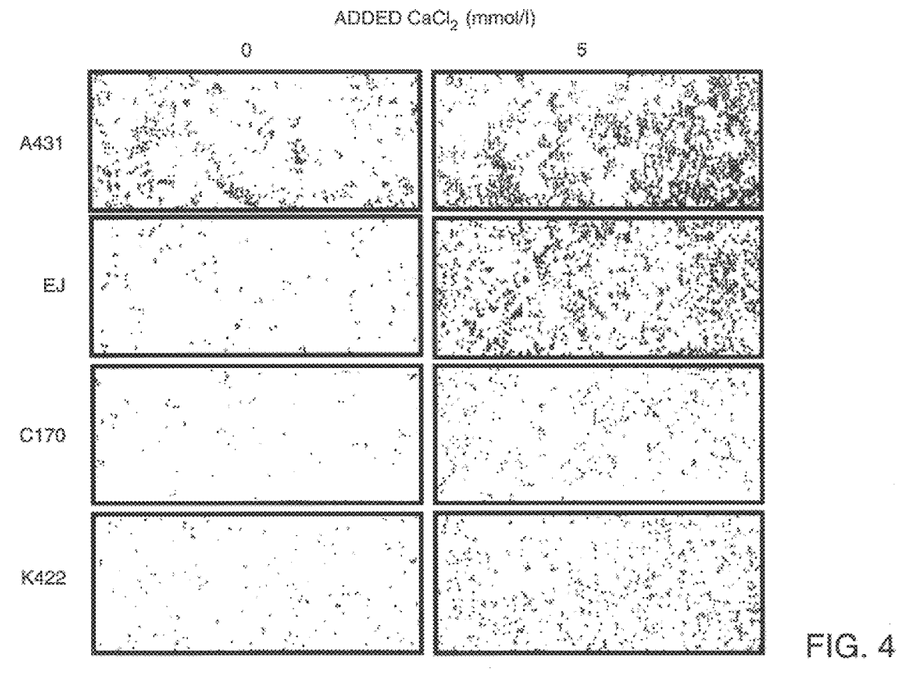
FIG. 4 is a series of photographs showing enhanced titre of co-precipitated retroviral vectors on human cell lines. 5 mmol/l $CaCl_2$ was added to an amphotropic β-galactosidase-transducing vector stock and, after a 30 minute incubation, 10 μl of the treated stock was used to infect a panel of human cell lines (2 hour incubation in a final volume of 2 mls). The β-galactosidase activity of the infected cells is recorded photographically (×20 magnification).

Enhanced titre of precipitated retroviral vectors on a panel of human cell lines Retroviral vector titres are routinely determined on murine NIH 3T3 cells but titration on human cells often gives much lower titres. To determine whether retroviral co-precipitation was a generally applicable method to enhance retroviral titres on human as well as murine cells, we infected a panel of human cell lines with untreated or co-precipitated amphotropic vectors (FIG. 4). In all cases, co-precipitation with 5 mmol/l $CaCl_2$ led to significant enhancement of retrovirus titre on the human cell lines which was independent of the presence of polybrene and which greatly exceeded the increase in titre achievable by the use of polybrene alone.

DISCUSSION

Despite the growing use of retroviral vectors in human gene therapy protocols, they give relatively low transduction frequencies on human cells and this presents a significant obstacle to progress.

In this application we describe a simple method to enhance the efficiency of ex vivo retroviral gene transfer. Retroviral vectors are harvested in DMEM, co-precipitated by the addition of 5 mmol/l $CaCl_2$ and the precipitate is applied to the target cell population. This procedure enhanced the apparent titre of ecotropic and amphotropic retroviral vector stocks far more efficiently than the use of polybrene, which is used routinely to assist retrovirus adsorption to target cell membranes. Compared to standard infection protocols using unprecipitated vectors, the titres of co-precipitated vectors were enhanced at least 5-fold, and sometimes as much as 50-fold, on all mouse and human cell lines tested. The enhanced titre of the co-precipitated vectors was not influenced by the addition of polybrene and was independent of the initial concentration of vector.

We explored alternative protocols in which varying concentrations of $CaCl_2$ were added to co-precipitate vectors while they were in contact with the target cells. An important point to emerge was that certain infection protocols were toxic to the target cells. This cytotoxic effect, which varied depending on the target cell type, was found to correlate with the abundance of the precipitate (in turn dependent on the amount of added $CaCl_2$) and the duration of target cell exposure. We therefore suggest that, where the use of vector co-precipitation is contemplated, the protocol should be optimised for the experimental system in question, ensuring that the target cells are not exposed to excessive amounts of precipitate for excessive periods of time.

Chromatography on calcium phosphate (hydroxyapatite) columns has previously been used to purify and concentrate viruses (Taverne et al 1958 J. Gen. Microbiol. 19 p451–461). Virus purification has also been attempted by adsorption on a precipitate formed by adding calcium chloride to a phosphate-containing solution (Stanley 1945 Science 101 p332–335). We propose that the enhancement of retrovirus titre observed in our experiments may be the result of retroviral vector particles binding to the calcium phosphate as it precipitates out of solution and then sedimenting rapidly onto the target cells—i.e. accelerating the kinerics of specific virus adsorption. Thus, when 5 mmol/l $CaCl_2$ was added to retroviral vectors harvested in DMEM, the visible precipitate was shown to contain around 99% of the vector particles and could be seen to settle spontaneously onto the target cells during the infection protocol. Low speed centrifugation of unprecipitated retroviral vectors onto their target cells has also been shown to enhance transduction efficiencies (Kotani et al 1994 Hum. Gene Ther. 5 p19–28).

Endocytosis, of precipitated retroviral vectors might also contribute their enhanced infectivity. The uptake of DNA by cultured cells is known to be enhanced when the nucleic acid is presented as a calcium phosphate-DNA co-precipitate (Graham & van der Eb 1973 Virology 52 p456–467, Chen and Okayarna 1987 Mol. Cell. Biol. 7 p2745–2752) and it is believed that the transfected DNA enters the ctyoplasm of the host cell by endocytosis before it is transferred to the nucleus. Hence, when optimising the concentrations of calcium and DNA required for their DNA transfection protocol, Graham & van der Eb (cited above) noted that the formation of a fine precipitate was important for success, perhaps because it was more efficiently endocytosed than coarse precipitates which were inactive.

However, in our experiments it was the abundance of the precipitate (which varied with the added concentration of $CaCl_2$) rather than its precise character that determined the degree to which transfer were enhanced, suggesting that endocytosis of the precipitate is not important for enhanced infectivity. Also, our experiments show that the ecotropic or amphotropic host range properties of the retroviral vectors were not altered by their co-precipitation, suggesting that the method works by facilitating the natural mechanism of binding and entry.

In summary the co-precipitation of retroviral vectors on calcium phosphate provides a very convenient method to maximise the efficiency of retroviral gene transfer

EXAMPLE 2

Materials and Methods

Viruses and cells.

The adenovirus AdAB21LacZ (Bett et al, 1993 J. Virol. 67 p5911–5921) was provided by Professor Frank L. Graham (McMaster University, Canada). This vector carries the LacZ gene which encodes the *E. coli* β-galactosidase enzyme. The virus was amplified on 293 cells (Graham et al 1977 J. Gen. Virol. 36 p59–72) which were grown in DMEM containing 10% foetal calf serum (PAA Biologics) and antibiotics at 37° C. in an atmosphere of 5% CO2.

Co-precipitation of adenoviral vectors.

A small volume of IM $CaCl_2$ was added to aliquots of an AdAB21LacZ adenoviral vector supernatant (that had been diluted 1000-fold in DMEM to a final titre of approximately $10^6$ β-galactosidase e.f.u.s per ml) to increase the concentration of $CaCl_2$ by 5 mmol/l. The $CaCl_2$-adjusted, diluted adenoviral vector supernatants were then incubated at room temperature for 30 minutes to allow precipitate formation. To harvest the precipitate, a 1 ml aliquot of the $CaCl_2$-treated vector supernatant was microfuged for 1 min at 13000 rpm, the cleared supernatant was removed and the pellet resuspended in 1 ml fresh DMEM.

Infection assay.

293 cells were seeded at $2\times10^3$ cells/well in six-well plates (Corning) and incubated at 37° C. overnight in their regular medium. Dilutions of (untreated or co-precipitated) β-galactosidase-transducing adenovirus vectors in 1 ml serum-free DMEM were added to cells for two hours. The adenoviral vector supernatant was removed, the cells washed once with PBS and incubated in regular medium overnight. $CaCl_2$-treated supernatants were mixed vigorously to ensure even suspension of the precipitate before aliquots were removed for dilution of direct application to target cells.

X-gal staining for detection of β-galactosidase activity was performed as previously described (Takeuchi et al, cited above). Cells were fixed with 0.5% glutaraldehyde in PBS at room temperature of 10 min, washed once with PBS and incubated overnight at 37° C. with a 0.21 μm-filtered solution containing 1 mg/ml 5-bromo-4-chloro-3-indoyl-β-D-galactoside (X-gal) in 5 mM potassium ferricyanide, 5 mM potassium ferrocyanide and 2 mM $MgCl_2$.

RESULTS 5 mmol/l $CaCl_2$ was added to aliquots of the AdAB21LacZ adenoviral vector stock (diluted 1 in 1000 in DMEM) and, after 30 minutes at room temperature, dilutions of the unprecipitated vector, the unpelleted precipitate and the pelleted precipitate, resuspended in DMEM were used to infect 293 cells. Infections were done in duplicate and X-gal staining was performed after overnight incubation (18 hours). Titres (X-gal enzyme-forming units per ml) were as follows:

| | |
|---|---|
| Unprecipitated vector | $10^6$ per ml |
| Unpelleted precipitate | $2 \times 10^6$ per ml |
| Resuspended pellet | $2 \times 10^6$ per ml |

DISCUSSION

This result demonstrates clearly that adenovirus vectors form a complex with the calcium phosphate crystals that form when $CaCl_2$ is added to a phosphate-containing solution, and that the vectors remain infectious while they are incorporated in the complex.

What is claimed is:

1. A method of delivering a nucleic acid to a target cell, comprising mixing a calcium salt precipitate with said nucleic acid, wherein said nucleic acid is packaged within a eukaryotic viral particle, so as to form a complex; and contacting said complex to said target cell.

2. The method of claim 1 wherein said viral particle is a retroviral particle.

3. The method of claim 1 wherein said calcium salt is calcium phosphate.

4. The method of claim 1, wherein said calcium salt precipitate comprises crystalline calcium phosphate.

5. The method of claim 1, wherein the target cell is a eukaryotic cell.

6. The method of claim 1, wherein the target cell is a mammalian cell.

7. The method of claim 1 wherein said eukaryotic viral particle is selected from the group consisting of retrovirus particle and adenovirus particle.

8. The method of claim 1, wherein said target cell is a human cell.

9. A method of delivering a nucleic acid to a target cell, comprising packaging said nucleic acid within a eukaryotic viral particle; mixing said nucleic acid containing eukaryotic viral particle with one or more components to enhance the efficiency of delivery of the nucleic acid to a target cell;

adding a calcium salt precipitate to said nucleic acid containing eukaryotic viral particle and said one or more components so as to form a complex; and contacting said complex to said target cell.

10. The method of claim 9, the method further comprising mixing said nucleic acid containing eukaryotic viral particle with an endosomolytic moiety prior to said adding step.

11. The method of claim 10, the method further comprising mixing said nucleic acid containing eukaryotic viral particle with an adenovirus particle prior to said adding step.

12. The method of claim 9 wherein said viral particle is a retroviral particle.

13. The method of claim 9 wherein said calcium salt is calcium phosphate.

14. The method of claim 9 wherein said calcium salt precipitate comprises crystalline calcium phosphate.

15. The method of claim 9 wherein the target cell is a eukaryotic cell.

16. The method of claim 15 wherein the target cell is a mammalian cell.

\* \* \* \* \*